United States Patent
Zhang et al.

(10) Patent No.: US 6,953,576 B2
(45) Date of Patent: Oct. 11, 2005

(54) METHOD OF MODULATING TUMOR IMMUNITY

(75) Inventors: Li Zhang, Toronto (CA); Kevin Young, Toronto (CA)

(73) Assignee: University Health Network, Toronto (CA)

(*) Notice: Subject to any disclaimer, the term of this patent is extended or adjusted under 35 U.S.C. 154(b) by 78 days.

(21) Appl. No.: 09/933,131

(22) Filed: Aug. 21, 2001

(65) Prior Publication Data

US 2002/0039576 A1 Apr. 4, 2002

Related U.S. Application Data

(60) Provisional application No. 60/226,573, filed on Aug. 21, 2000.

(51) Int. Cl.$^7$ .......................... A01N 63/00; A61K 35/26; C12N 5/00
(52) U.S. Cl. .................. 424/93.7; 424/577; 435/373; 435/375
(58) Field of Search ................ 424/93.7, 577; 435/373, 375, 41

(56) References Cited

PUBLICATIONS

Chatterjee et al. Cancer Immunol. Imunother., 1994, v.38, pp. 75–82.*

Dermer Biotechnology 12: 320, 1994.*

Sussman et al.Annals of Surgical Incology, 1994, v.1 p296–306.*

Klingemann J. of Hematotheraphy and Stem Cell Research, 2001, v.10, p23–26.*

* cited by examiner

*Primary Examiner*—Christina Chan
*Assistant Examiner*—Michail Belyavskyi
(74) *Attorney, Agent, or Firm*—Bereskin & Parr; Micheline Gravelle (57) ABSTRACT

Novel cells and molecules involved in tumor immunity are disclosed. The novel cells are regulatory T-cells having the phenotype $CD3^+\alpha\beta\text{-TcR}^+CD4^-CD8^-CD44^-CD28^-NK1.1^-$. The regulatory cells express Ly6A and osteopontin while non-regulatory cells do not.

5 Claims, 7 Drawing Sheets a.

Schematic model of 1B2+DN T cell mediated cytotoxicity.

FIGURE 7

METHOD OF MODULATING TUMOR IMMUNITY

This application claims the benefit under 35 USC §119(e) of U.S. provisional application No. 60/226,573 filed Aug. 21, 2000.

FIELD OF THE INVENTION

The present invention relates to methods and compositions for modulating tumor immunity.

BACKGROUND OF THE INVENTION

An anti-leukemia/lymphoma effect can be achieved by infusing allogeneic lymphocytes from bone marrow, blood or spleen of healthy donors into tumour bearing recipients (Bortin et al (1989); Korngold et al. (1994)). The ability of infused lymphocytes to prevent leukemia relapse is termed graft-versus-leukemia (GVL), and is often attributed to the allogeneic portion of the infused lymphocytes. However, the infused foreign lymphocytes, can also respond to the major and minor histocompatibility (MHC and mH, respectively) antigens expressed on host cells and cause graft versus host disease (GVHD) which represents a major factor responsible for the death of recipients (Sprent et al. (1986); Ferrara et al. (1991)). In class I mismatched models, $CD8^+$ T cells contribute significantly to GVHD (Korngold et al. (1985); Champlin et al. (1991)). In order to reduce the severity of GVHD, lymphocytes from donors that are matched for MHC antigens with the recipients have been used in conjunction with non-specific immunosuppression. Although these approaches decrease the incidence and severity of GVHD, they also reduce marrow engraftment and increase leukemia relapse (Korngold et al. (1994); Kolb et al. (1995); Barrett et al. (1996)). While multiple cell types, including $CD4^+$, $CD8^+$ and NK T cells have been shown to play a role in GVL (Champlin (1992); Imamura et al. (1996); Zeis et al. (1997)); Hauch et al. (1990); van Lochem et al. (1992); Sykes et al. (1994); Palathumpat et al. (1992); Palathumpat et al. (1995)), it remains uncertain whether the cells that contribute to GVHD are distinct from those that kill tumour cells (Champlin (1992); van Lochem et al. (1992); Apperley et al. (1986); Prentice et al. (1984); Horowitz et al. (1990); Pan et al. (1999)). Consequently, a goal of bone marrow tranplantation is to identify and augment those cells with a beneficial GVL effect that do not contribute to GVHD.

Accumulating evidence indicate that T regulatory (Tr) lymphocytes play an important role in down-regulation of immune responses to self or allogeneic antigens (Qin et al. (1993); Groux et al. (1997); Zhang et al. (2000); Han et al (1996); Ierino et al. (1999); Cobbold et al. (1998) Bushell et al. (1999); Baxter et al. (1997); Lancaster et al. (1985); Chai et al. (1999); Zhai et al. (1999); Sakaguchi (2000); Roncarolo et al. (2000)). Whether Tr cells play a role in GVHD/GVL, however, remains unclear. The inventors and others have demonstrated that pre-transplantation donor-specific transfusion (DST) of one MHC class I or class II mismatched lymphocytes leads to permanent acceptance of the skin or cardiac allografts of the lymphocyte donor origin (Yang et al. (1999); van Twuyver et al. (1989); van Twuyver et al. (1990)). Because all third party allografts were promptly rejected by the recipients after DST, it indicates that the tolerance induced by one MHC locus-mismatched lymphocytes is antigen-specific, and the recipients retained their immune responses to other alloantigens. Furthermore, from the recipients who have received DST and permanently accepted donor skin allografts, the inventors have recently identified a novel $CD4^-CD8^-$ double negative (DN) Tr cells which differs from any previously reported Tr cells in terms of their surface marker expression, cytokine profile and mechanism of suppression (Zhang et al. (2000)). The inventors also demonstrated that the DN Tr cells are able to kill activated $CD8^+$ T cells that carry the same TCR specificity (Zhang et al. (2000)).

There is a need in the art to identify cells involved in tumor immunity that are useful in developing anti-cancer therapies.

SUMMARY OF THE INVENTION

The inventors have demonstrated that anti-lymphoma effects can be achieved in the absence of GVHD by a single injection of either viable allogeneic splenocytes or double negative regulatory T cells (DN Tr cells), which differ in one MHC class I locus with recipients. Tolerance of the host is permanent and does not need any non-specific toxic immunosuppressive drugs. Furthermore, the inventors demonstrated that DN Tr cells are able to function as a double-edged sword to kill both syngeneic anti-host $CD8^+$ T cells and allogeneic lymphoma cells. These findings reveal for the first time the dual role of Tr cells both in inhibiting GVHD and blocking the development of leukemia. They also provide a novel concept for the treatment of lymphoma/leukemia by allogeneic lymphocytes.

The novel double negative regulatory T-cells isolated by the inventors are $CD3^+\alpha\beta$-$TcR^+CD4^-CD8^-CD44^-CD28^-NK1.1^-$. The cells do not express IL-2, IL-4, IL-10 and IL-13 but do express IFN-$\gamma$, TNF-$\alpha$ and TGF-$\beta$ mRNA after activation. Treatment of the regulatory T-cells with IL-10, cyclosporin A or anti-IFN-$\gamma$ antibodies abrogates suppression by the cells.

Accordingly, the present invention provides the use of the novel regulatory cells to modulate tumor immunity or graft versus host disease (GVHD). Accordingly, the present invention provides a method of inhibiting tumor cell growth or proliferation comprising administering an effective amount of (i) a regulatory T-cell having the phenotype $CD3^+\alpha\beta$-$TcR^+CD4^-CD8^-CD44^-CD28^-NK1.1^-$, or (ii) an agent that can induce or activate the regulatory T-cell to an animal in need of such treatment.

In one embodiment, the present invention provides a method of preventing or treating cancer comprising administering an effective amount of a regulatory T cell having the phenotype $CD3^+\alpha\beta$-$TcR^+CD4^-CD8^-CD44^-CD28^-NK1.1^-$ to an animal in need of such treatment.

The present inventors have also found that the proteins Ly6A and osteopontin are expressed on the above described regulatory T-cells but not on non-regulatory cells. Further, they have also shown that blocking Ly6A or osteopontin abolishes the effect of these cells.

Accordingly, the present invention provides a method of inhibiting tumor cell growth comprising administering an effective amount of an Ly6A protein, a nucleic acid sequence encoding an Ly6A protein, osteopontin or a nucleic acid sequence encoding osteopontin to an animal in need of such treatment.

The invention also includes pharmaceutical compositions containing the DN regulatory cells, agents that induce or activate the regulatory cells, antibodies to the novel cells, Ly6A proteins, nucleic acids encoding Ly6A protein, osteopontin or a nucleic acid sequence encoding osteopontin for use in modulating tumor immunity or graft versus host disease.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 2: No histological signs of leukemia or GVHD following challenge with $L^{d+}$ allogeneic splenocytes and a lethal dose of A20 lymphoma. i. Gross picture of two mouse livers: Scid$_{F1}$ mice were injected with $10^5$ A20 B lymphoma cells. Four weeks after tumour inoculation, the livers were harvested (left panel). The liver is greatly enlarged, has a bulging surface and rounded edges. This liver is diffusely infiltrated by tumour cells as shown in ii. The liver on the right panel is from another Scid$_{F1}$ mouse that received the same number of A20 cells plus $3\times10^7$ $2C_{F1}$ splenocytes. It is normal in size, shape and color. ii. and iii. Histopathology of livers of Scid$_{F1}$ mice (Hematoxylin and eosin stain ×300). Scid$_{F1}$ mice were injected with $10^5$ A20 B lymphoma cells. Four weeks after tumour inoculation, livers was harvested (see panel i, left). There is very diffuse infiltration by large malignant tumour cells which completely replaces the normal liver architecture. Most of the tumour cells are mononuclear, pleomorphic and had irregular hyperchromatic nuclei. Many of the smaller irregular cells present are undergoing necrosis, mitoses and atypical mitoses are frequent. Occasional tumour giant cells are present. The overall appearance is typical of large cell lymphoma (ii). Scid$_{F1}$ mice were intravenously injected with $10^5$ A20 cells plus $3\times10^7$ $2C_{F1}$ splenocytes (liver shown in right panel of i). The liver histology is near normal. The hepatocytes, liver cell cords, portal and venous structures are all normal. There is a slight increase in sinusoidal cells most of which are small lymphocytes. There is no evidence of afypia and no malignant cells (iii).

FIG. 3: (a) Indefinite survival of normal mice reconstituted with $L^d$-mismatched splenocytes. (B6×BALB/c)$_{F1}$ mice were lethally irradiated (8.5 Gy) with no further treatment (▲, n=5), or reconstituted with $40\times10^6$ $L^d$ mismatched (B6×dm2)$_{F1}$ lymphocytes (♦, n=13). Additionally, (B6×BALB/c)$_{F1}$ mice were either given a lethal dose ($10^5$ cells) of A20 lymphoma alone (■, n=8), or lethally irradiated and reconstituted with $40\times10^6$ $L^d$ mismatched (B6× dm2)$_{F1}$ mouse lymphocytes together with a lethal dose of A20 lymphoma (▼, n=8). Survival and signs of GVHD and tumour were monitored for more than 150 days. (b) No histological signs of GVHD in non-transgenic mice reconstituted with $L^d$-mismatched splenocytes. (Hematoxylin and Eosin stain ×300). (B6×BALB/c)$_{F1}$ mice were lethally irradiated (8.5 Gy) and reconstituted with $3\times10^7$ splenocytes either from B6 (semi-allogeneic, top panel), (B6×dm2)$_{F1}$ ($L^d$-mismatched non-transgenic, middle panel) or $2C_{F1}$ ($L^d$-mismatched transgenic, bottom panel). Liver histology is shown at 100 days after infusion of allogeneic cells. The top panel shows infiltrating mononuclear cells, proliferation in bile ducts, and abnormal portal and venous structure, a typical lesion of chronic graft versus host disease in the liver. The middle and bottom panel show that the liver histology is normal. The hepatocytes, liver cell cords, portal and venous structures are normal. There is no evidence of graft versus host disease.

FIG. 4: Expansion of DN T cells and elimination of anti-host CD8$^+$ T cells following infusion of $L^d$-mismatched $2C_{F1}$ cells. Scid$_{F1}$ mice were injected with either $3\times10^7$ spleen cells from $2C_{F1}$ mice alone (a) or in combination with $10^5$ A20 lymphoma cells (b) as described earlier. Mice were sacrificed at various time points as indicated, and the total number of lymphocytes in the spleen was counted. The spleen cells were simultaneously stained with 1B2-FITC and CD8-PE and analyzed by FACS. Data shown is total number of splenic 1B2$^+$CD8$^+$ (■) and 1B2+CD8− (▼) cells calculated by multiplying the percent positive cells by the total number of spleen cells. (c) DN T cells from mice reconstituted with $L^d$-mismatched normal spleen cells suppress proliferation of naïve anti-host CD8$^+$ T cells. (B6×BALB/c)$_{F1}$ mice were lethally irradiated (8.5 Gy) and reconstituted with $40\times10^6$ (B6×dm2)$_{F1}$ splenocytes. Recipient mice were monitored for signs of GVHD for 30 weeks, and CD3$^+$CD4$^-$CD8$^-$ T cells were then purified from the spleens of recipient mice using FACS. Varying numbers (as indicated) of DN T cells were incubated together with 1000 1B2$^+$CD8$^+$ responder T cells or alone. The proliferation of DN T cells alone or the DN/CD8$^+$ cultures was measured by [$^3$H]-TdR incorporation after 4 days of culture. The results show the proliferation of DN/CD8$^+$ cells minus background proliferation of DN T cells alone.

FIG. 5: DN T cell mediated cytotoxicity to anti-host 1B2$^+$CD8$^+$ T cells and A20 lymphoma cells. (a) Anti-$L^d$ DN T cell clones were stimulated as described previously (Zhang et al. (2000), and then added at various ratios (as indicated) to 96 well plates. In vitro activated anti-$L^d$ 1B2$^+$CD8$^+$ T cells (■) and anti-HY T370$^+$CD8$^+$ T cells (▼) were labeled with 10 μCi $^3$H-TdR overnight, and used as targets (10,000 cells/well). Cells were harvested after 18 hours, and specific killing of target cells was determined. Results are representative of 3 independent experiments. (b) DN T cells kill A20 tumour cells in vitro. DN T line (CNO4) was used as effector cells, and A20 (■, $L^{d+}$) and control BW5147 (▼, $L^{d-}$) tumour cells were labeled with [$^3$H]-TdR and used as targets. Specific killing of target cells was determined. Results are representative of 2 independent experiments.

FIG. 6: DN T cells suppress growth of A20 tumour cells in vivo. (a) 1B2$^+$DN Tr cell clones (L12.2 and CN04) were grown and purified in vitro. (B6×BALB/c) mice were injected i.v. with either a lethal dose of A20 cells alone (▲) or together with $5\times10^6$ of either L12.2(■) or CN04 (▼) DN Tr T cell clones. Survival and clinical signs of GVHD was monitored for more than 150 days. (b) Absence of pathohistologic signs of tumour or GVHD after co-injection of A20 tumour cells with DN T cells. (B6×BALB/c) mice were challenged with a lethal dose of A20 tumour alone or together with DN T cells as described in (a). Mice were sacrificed after 30 or 100 days and the major organs were examined for evidence of tumour infiltrates. Mice injected with A20 alone (top panel) showed dense tumour infiltrates which completely replaced the normal liver structure. Mice that were co-injected with DN T cells had normal liver structure with no infiltrating tumour cells or signs of GVHD. Data shown is for 30 days (top panel) and 100 days (bottom panel).

DETAILED DESCRIPTION OF THE INVENTION

The inventors have show that reconstitution of immuno-deficient mice with spleen cells from one MHC class I $L^d$ mismatched donors leads to an indefinite survival of all the recipients free of GVHD and tumour after being challenged with a lethal dose of lymphoma. To study the mechanisms involved in this phenomenon, the fate of infused donor cells in vivo was monitored. The number of anti-host $CD8^+$ cells was initially augmented, but quickly diminished and remained very low throughout the rest of the experimental period. Interestingly, a marked (>30 fold) increase of DN Tr cells in the periphery of recipient mice was observed, which remained elevated throughout the experimental period. Moreover, the DN Tr cells isolated from reconstituted mice could suppress the proliferation of anti-host T cells, and the DN Tr cell lines generated in vitro could specifically kill activated anti-host $CD8^+$ T cells. These findings suggest that DN Tr cells may prevent GVHD by directly killing anti-host $CD8^+$ T cells in vivo. Furthermore, the inventors demonstrated that DN Tr were cytotoxic to lymphoma cells in vitro. When co-injected with a lethal dose of lymphoma into naive mice, the DN Tr cells were capable of preventing leukemia onset in all recipients. In conclusion, the infusion of one class I MHC locus mismatched splenocytes together with a lethal dose of lymphoma cells does not cause GVHD or leukemia, but results in an expansion of DN Tr cells in the periphery of the recipients. These DN Tr cells are cytotoxic to both anti-host $CD8^+$ T cells and leukemia cells, indicating a dual role for DN Tr cells in the prevention of both GVHD and leukemia.

The DN regulatory T-cells of the invention are distinguished from previously described regulatory cells as they possess a unique phenotype and express a unique array of cytokines. In particular, the novel cells are $CD3^+\alpha\beta$-$TCR^+$ $CD4^-CD8^-CD25^+CD28^-CD30^+CD44^-NK1.1^-$. These cell surface markers distinguish the cells from any previously described T-cell subset such as activated helper, cytotoxic or memory T-cells. The novel regulatory cells are also distinguished from bone marrow derived $CD4^-CD8^-$T-cells which express NK1.1 and from $CD4^-CD8^-$ T-cells described by others. The novel regulatory cells do not express IL-2, IL-4, IL-10 and IL-13 but do express IFN-$\gamma$ and TGF-$\beta$ mRNA after activation which distinguish them from Th1, Th2 or Th3/Tr1 cells.

The regulatory cells having the phenotype $CD3^+\alpha\beta$-$TcR^+$ $CD4^-CD8^-CD44^-CD28^-NK1.1^-$ are sometimes referred to herein as "the regulatory cells of the invention", "the DN regulatory T cells" or "the DN Tr cells".

I. Methods of Inhibiting Tumor Cell Growth/Treating Cancer

Accordingly, the present invention provides a method of inhibiting tumor cell growth or proliferation comprising administering an effective amount of (i) a regulatory T-cell having the phenotype $CD3^+\alpha\beta$-$TcR^+CD4^-CD8^-CD44^-$ $CD28^-NK1.1^-$, or (ii) an agent that can induce or activate the regulatory T-cell to an animal in need of such treatment. The present invention also includes a use of (i) a regulatory T-cell having the phenotype $CD3^+\alpha\beta$-$TcR^+CD4^-CD8^-$ $CD44^-CD28^-NK1.1^-$, or (ii) an agent that can induce or activate the regulatory T-cell to prepare a medicament to inhibit tumor cell growth or proliferation. The invention further includes a use of (i) a regulatory T-cell having the phenotype $CD3^+\alpha\beta$-$TcR^+CD4^-CD8^-CD44^-CD28^-NK1.1^-$, or (ii) an agent that can induce or activate the regulatory T-cell to inhibit tumor cell growth or proliferation.

(i) Administering DN Tr Cells

In one embodiment, the method involves administering DN Tr cells that are generated in vitro. The cells may be isolated from normal animals, for example by labelling T-cells and sorting for cells containing the desired phenotype using a FACS sorter. The inventors have demonstrated that the novel regulatory cells require IL-2, IL-4 to proliferate and to suppress. The inventors have further developed methods to activate and expand antigen-specific regulatory T cells in vitro by stimulating the novel regulatory T cells with one class I mismatched allogeneic lymphocytes in the presence of IL-2 and IL-4. Accordingly, IL-2 and IL-4 can be used to increase the number and improve the function of the novel regulatory cells. The regulatory cells of the invention can be activated and expanded in vitro by stimulating the cells with antigens in forms such as purified peptides, soluble proteins, plasmid expressing cDNA encoding specific antigens, cell lines expressing specific antigens (EBV transformed cell lines, dendritic cells, fibroblasts transfected with specific antigens such as foreign MHC molecules), tumor antigens and molecules that cause autoimmune diseases and allergy.

The inventors have also shown that injection of the regulatory T cells that are generated in vitro into animals can prevent death caused by injection of lethal dose of tumor cells in the absence of GVHD. Accordingly, in vitro cultured regulatory T cells can be used in the treatment of leukemia, lymphomas and other malignant diseases.

(ii) Administering Agents That Stimulate DN Tr Cells

In another embodiment, the method of inhibiting tumor cell growth involves administering an agent that can induce or activate the DN regulatory T cells in vivo. Such agents include but are not limited to, cytokines, antigens, antibodies to the DN Tr cells that can activate the cells and one MHC Class I mismatched allogeneic lymphocytes as herein described.

The cytokine can be any cytokine that can stimulate or activate the DN Tr cells such as IL-2 and IL-4 and IFN-$\gamma$.

The antigens used to stimulate the DN Tr cells can be any antigen including, but not limited to, tumor antigens or allogeneic lymphocytes with one MHC Class I mismatch with the recipient. In particular, the inventors have identified the methods to increase the number of the novel regulatory T cells in immunodeficient recipients by infusion of one MHC class I locus mismatched lymphocytes, which lead to elimination of tumor cells in the absence of GVHD. Accordingly, the present invention also provides a method of inhibiting tumor cell growth comprising administering to an animal in need thereof allogeneic lymphocytes containing a mismatch at one MHC Class I locus with the animal.

The antibodies can be any antibody that can stimulate or activate the DN Tr cells. The inventors have prepared monoclonal antibodies (mAbs) generated by immunization of animals with regulatory T cells of the invention. The inventors have so far generated 25 mAbs that can specifically bind to the surface of regulatory T cells some of which enhance growth of the regulatory T cells.

Antibodies to the DN Tr cells may also be prepared using techniques known in the art such as those described by Kohler and Milstein, Nature 256, 495 (1975) and in U.S. Pat. Nos. RE 32,011; 4,902,614; 4,543,439; and 4,411,993, which are incorporated herein by reference. (See also Monoclonal Antibodies, Hybridomas: A New Dimension in Biological Analyses, Plenum Press, Kennett, McKeam, and Bechtol (eds.), 1980, and Antibodies: A Laboratory Manual, Harlow and Lane (eds.), Cold Spring Harbor Laboratory Press, 1988, which are also incorporated herein by reference). Within the context of the present invention, antibodies are understood to include monoclonal antibodies, polyclonal antibodies, antibody fragments (e.g., Fab, and F(ab')$_2$) and recombinantly produced binding partners.

Accordingly, the invention also includes the use of mAbs to the DN Tr cells and their therapeutic modifications in prevention and treatment of cancer. Modifications of mAbs include generation of recombinant mAbs fused with human immunoglobulin Fc portion, conjugate mAbs with enzymes, isotopes etc.

The inventors have postulated novel mechanisms by which the regulatory T cells prevent GVHD and promote anti-tumor response. After bone marrow transplantation mature donor T cells (CD4$^+$ and CD8$^+$) will recognize allo MHC expressed on the host, be activated and express high level of Fas. These activated donor T cells will destroy target cells and tissues that express the host alloantigens and cause GVHD. The inventors have demonstrated that the novel regulatory T cells constitutively express a high level of Fas ligand. Upon encountering antigen-presenting cells (APC), the regulatory T cells can "steal" host alloantigens from the surface of APC through the anti-host TCR, and turn themselves into killer cells. Because the regulatory T cells express the "stolen" host alloantigens on their surface, they can attract the activated anti-host cytotoxic T cells. Once the anti-host cytotoxic T cells recognised the alloantigens on the regulatory T cells, the latter will send death signals through Fas ligand to the former. Unlike the anti-host cytotoxic T cells, which kill target cells through perforin-mediated pathway, the killing mediated by the regulatory T cells requires direct cell-cell contact and depends on Fas-FasL interaction. Most host tissues, although they express MHC class I molecules, do not express Fas, and will not be destroyed directly by the regulatory T cells. Therefore the regulatory T cell themselves do not cause GVHD. On the other hand, the tumor cells, such as B cell lymphoma, express both recipients MHC class I and Fas. The regulatory T cells can recognize the MHC class I expressed on tumor cells through their specific TCR, and send death signals to tumor cells through Fas ligand to cause death of tumor cells and prevent death caused by lymphoma.

The present inventors have isolated several genes that are expressed in the novel regulatory cells of the invention but are not expressed in non-regulatory cells. In particular, the inventors have determined that Ly6A is expressed on the novel regulatory cells. Ly6A is a glycosyl phosphatidylinositol (GPI)-anchored cell surface molecule expressed on most peripheral lymphocytes, thymocytes and other cells. Incubating the novel regulatory cells with IL-10 (which converts the regulatory phenotype into a non-regulatory one reduces the expression of Ly6A. Further, blocking Ly6A expression with an antisense oligonucleotide abolishes suppression by the novel regulatory cells. These results suggest that Ly6A may act to down regulate lymphocyte responses. Consequently, administering Ly6A may be used to inhibit tumor cell growth. Accordingly, the present invention provides a method of inhibiting tumor cell growth comprising administering an effective amount of an Ly6A protein or a nucleic acid encoding an Ly6A protein to an animal in need thereof.

The term "Ly6A protein" as used herein includes the full length Ly6A protein as well as fragments or portions of the protein. Preferred fragments or portions of the protein are those that are sufficient to suppress an immune response. The Ly6A protein also includes fragments that can be used to prepare antibodies.

The Ly6A protein may be prepared as a soluble fusion protein. The fusion protein may contain the extracellular domain of Ly6A linked to an immunoglobulin (Ig) Fc Region. The Ly6A fusion may be prepared using techniques known in the art. Generally, a DNA sequence encoding the extracellular domain of Ly6A is linked to a DNA sequence encoding the Fc of the Ig and expressed in an appropriate expression system where the Ly6A-FcIg fusion protein is produced. The Ly6A protein may be obtained from known sources or prepared using recombinant DNA techniques. The protein may have any of the known published sequences for Ly6A. The protein may also be modified to contain amino acid substitutions, insertions and/or deletions that do not alter the immunosuppressive properties of the protein. Conserved amino acid substitutions involve replacing one or more amino acids of the Ly6A amino acid sequence with amino acids of similar charge, size, and/or hydrophobicity characteristics. When only conserved substitutions are made the resulting analog should be functionally equivalent to the Ly6A protein. Non-conserved substitutions involve replacing one or more amino acids of the Ly6A amino acid sequence with one or more amino acids which possess dissimilar charge, size, and/or hydrophobicity characteristics.

The Ly6A protein may be modified to make it more therapeutically effective or suitable. For example, the Ly6A protein may be cyclized as cyclization allows a peptide to assume a more favourable conformation. Cyclization of the Ly6A peptides may be achieved using techniques known in the art. In particular, disulphide bonds may be formed between two appropriately spaced components having free sulfhydryl groups. The bonds may be formed between side chains of amino acids, non-amino acid components or a combination of the two. In addition, the Ly6A protein or peptides of the present invention may be converted into pharmaceutical salts by reacting with inorganic acids including hydrochloric acid, sulphuric acid, hydrobromic acid, phosphoric acid, etc., or organic acids including formic acid, acetic acid, propionic acid, glycolic acid, lactic acid, pyruvic acid, oxalic acid, succinic acid, malic acid, tartaric acid, citric acid, benzoic acid, salicylic acid, benzenesulphonic acid, and tolunesulphonic acids.

The inventors have also demonstrated that osteopontin is highly expressed on regulatory but not on non-regulatory T cells and incubation of anti-osteopontin antibody can reverse the suppressive function of the regulatory T cells. Consequently, administering osteopontin may be used to inhibit tumor cell growth. According, the present invention provides a method of inhibiting tumor cell growth comprising administering an effective amount of an osteopontin or a nucleic acid encoding an osteopontin to an animal in need thereof.

The term "osteopontin protein" as used herein includes the full length osteopontin protein as well as fragments or portions of the protein. Preferred fragments or portions of the protein are those that are sufficient to suppress an immune response. The osteopontin protein also includes fragments that can be used to prepare antibodies.

The osteopontin protein may be prepared as a soluble fusion protein. The fusion protein may contain the extracellular domain of osteopontin linked to an immunoglobulin (Ig) Fc Region. The osteopontin fusion may be prepared using techniques known in the art. Generally, a DNA sequence encoding the extracellular domain of osteopontin is linked to a DNA sequence encoding the Fc of the Ig and expressed in an appropriate expression system where the osteopontin—FcIg fusion protein is produced. The osteopontin protein may be obtained from known sources or prepared using recombinant DNA techniques. The protein may have any of the known published sequences for osteopontin. The protein may also be modified to contain amino acid substitutions, insertions and/or deletions that do not alter the immunosuppressive properties of the protein. Conserved amino acid substitutions involve replacing one or more amino acids of the osteopontin amino acid sequence with amino acids of similar charge, size, and/or hydrophobicity characteristics. When only conserved substitutions are made the resulting analog should be functionally equivalent to the osteopontin protein. Non-conserved substitutions involve replacing one or more amino acids of the osteopontin amino acid sequence with one or more amino acids which possess dissimilar charge, size, and/or hydrophobicity characteristics.

The osteopontin protein may be modified to make it more therapeutically effective or suitable. For example, the osteopontin protein may be cyclized as cyclization allows a peptide to assume a more favourable conformation. Cyclization of the osteopontin peptides may be achieved using techniques known in the art. In particular, disulphide bonds may be formed between two appropriately spaced components having free sulfhydryl groups. The bonds may be formed between side chains of amino acids, non-amino acid components or a combination of the two. In addition, the osteopontin protein or peptides of the present invention may be converted into pharmaceutical salts by reacting with inorganic acids including hydrochloric acid, sulphuric acid, hydrobromic acid, phosphoric acid, etc., or organic acids including formic acid, acetic acid, propionic acid, glycolic acid, lactic acid, pyruvic acid, oxalic acid, succinic acid, malic acid, tartaric acid, citric acid, benzoic acid, salicylic acid, benzenesulphonic acid, and tolunesulphonic acids.

Administration of an "effective amount" of the active agent (i.e., DN regulatory T cells, agents that induce or activate the DN regulatory cells, antibodies, osteopontin or Ly6A protein or a nucleic acid molecule encoding Ly6A or osteopontin) is defined as an amount effective, at dosages and for periods of time necessary to achieve the desired result (e.g. inhibition or reduction of tumor cell growth). The effective amount of the active agent may vary according to factors such as the disease state, age, sex, and weight of the animal. Dosage regima may be adjusted to provide the optimum therapeutic response. For example, several divided doses may be administered daily or the dose may be proportionally reduced as indicated by the exigencies of the therapeutic situation.

The term "animal" as used herein includes all members of the animal kingdom including humans. The animal is preferably an animal with cancer or predisposed to getting cancer.

The term "inhibiting tumor cell growth" means that there is an inhibition or reduction in the growth, proliferation or metastasis of a tumor as compared to the growth observed in the absence of administering a DN Tr cell, an agent that activates a DN Tr cell, or Ly6A or osteopontin.

The term "tumor" includes any cancer, neoplasm or malignant disease including both solid and non-solid cancers. The method may be used to treat any cancer or malignant disease including, but not limited to, leukemias, lymphomas (Hodgkins and non-Hodgkins), liver cancer, lung cancer, plasmacytomas, histiocytomas, melanomas, adenomas, sarcomas, carcinomas of solid tissues, hypoxic tumours, squamous cell carcinomas, genitourinary cancers such as cervical and bladder cancer, hematopoietic cancers, head and neck cancers, and nervous system cancers.

Because the regulatory T cells express high level of Fas ligand and are able to recognize the host HLA alloantigens expressed on tumor cells through their TCR, they should be able to kill tumor cells that express both host HLA class I molecules and Fas as the inventors have demonstrated. In case that tumor cells do not express HLA class I antigen or Fas, the regulatory T cells will be co-injected with mature donor $CD8^+$ T cells. As the regulatory T cells can kill $CD8^+$ T cells that are activated by the same alloantigen, activated donor $CD8^+$ T cells that can specifically recognize host antigen and cause GVHD will be killed by the regulatory T cells though the mechanisms the inventors have demonstrated. However, the donor $CD8^+$ T cells that are activated by tumor antigens will not be affected by regulatory T cells. Therefore tumor cells can be eliminated by co-injected tumor-specific $CD8^+$ T cells through a perforin-dependant pathway. For hematopoietic malignancies, the regulatory T cells will be injected intravenously, for solid tumors, regulatory T cells will be injected both intravenously and at the side of tumor, preferably after surgical removal of the tumor.

The present invention also provides a method of preventing or treating cancer comprising administering an effective amount of (i) a regulatory T-cell having the phenotype $CD3^+\alpha\beta\text{-TcR}^+CD4^-CD8^-CD44^-CD28^-NK1.1^-$, or (ii) an agent that can induce or activate the regulatory T-cell to an animal in need of such treatment. In one embodiment, the regulatory T cells may be induced with IL-2 and IL-4 or by an antibody that stimulates the regulatory cells.

The term "treating cancer" includes, but is not limited to, alleviation or amelioration of one or more symptoms or conditions of cancer, diminishment of extent of disease, stabilized (i.e. not worsening) state of disease, preventing spread of disease, delay or slowing of disease progression, amelioration or palliation of the disease state, remission (whether partial or total), whether detectable or undetectable and/or prolonging survival as compared to expected survival if not receiving treatment.

II. Compositions

The invention also includes pharmaceutical compositions containing the DN regulatory T cells, agents that induce or activate the DN Tr cells, the antibodies to the T cells, Ly6A or osteopontin proteins or nucleic acids for use in treating cancer.

Such pharmaceutical compositions can be for intralesional, intravenous, topical, rectal, parenteral, local, inhalant or subcutaneous, intradermal, intramuscular, intrathecal, transperitoneal, oral, and intracerebral use. The composition can be in liquid, solid or semisolid form, for example pills, tablets, creams, gelatin capsules, capsules, suppositories, soft gelatin capsules, gels, membranes, tubelets, solutions or suspensions.

The pharmaceutical compositions of the invention can be intended for administration to humans or animals. Dosages to be administered depend on individual needs, on the desired effect and on the chosen route of administration.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985).

On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other agents such as chemotherapeutic agents, immunosuppressive drugs or antibodies to enhance immune tolerance or immunostimulatory agents to enhance the immune response.

In one embodiment, the pharmaceutical composition for use in treating cancer comprises an effective amount of an Ly6A protein or osteopontin in admixture with a pharmaceutically acceptable diluent or carrier. The Ly6A protein or osteopontin is preferably prepared as an immunoadhesion molecule in soluble form which can be administered to the patient. The composition preferably contains Ly6A proteins or osteopontin in soluble form which may be injected intravenously or perfused directly at the site of the tumor.

In another embodiment, the pharmaceutical composition for use in treating cancer comprises an effective amount of a nucleic acid molecule encoding an Ly6A protein or osteopontin in admixture with a pharmaceutically acceptable diluent or carrier.

The nucleic acid molecules of the invention encoding an Ly6A or osteopontin protein may be used in gene therapy to treat cancer. Recombinant molecules comprising a nucleic acid sequence encoding an Ly6A or osteopontin protein, or fragment thereof, may be directly introduced into cells or tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes. Recombinant molecules may also be delivered in the form of an aerosol or by lavage. The nucleic acid molecules of the invention may also be applied extracellularly such as by direct injection into cells. The nucleic acid molecules encoding Ly6A or osteopontin are preferably prepared as a fusion with a nucleic acid molecule encoding an immunoglobulin (Ig) Fc region. As such, the Ly6A or osteopontin protein will be expressed in vivo as a soluble fusion protein.

The following non-limiting examples are illustrative of the present invention:

EXAMPLE

Example 1

Materials and Methods

Mice. C57BL/6 (B6), (B6×BALB/c)$_{F1}$, and BALB/c H-2-dm2 (dm2) mice were purchased from Jackson Laboratories (Bar Harbor, Me.). A breeding stock of 2C transgenic mice was kindly provided by Dr. Dennis Y. Loh (Sha et al. (1988)). 2C Tg mice carry functionally re-arranged TCR α-(one copy) and β-chain (eight copies) transgenes from a cytotoxic T cell clone 2C which is specific for class I MHC Ag L$^0$ (Sha et al. (1988)). The specificity for L$^d$ requires the transgenic α and β chains (Sha et al. (1988); Sha et al. (1988)). The 2C clonotypic TCR is recognized by the mAb 1B2 (Kranz et al. (1984)). 2C transgenic mice were first backcrossed onto B6 mice for more than 15 generations to obtain the transgene on a B6 background and then bred with dm2 mice (a BALB/c L$^d$ loss mutant). The trangene positive (H-2$^{b/d}$, L$^{d-}$; 1B$^{2+}$) offspring were used as lymphocyte donors. C.B-17 Scid (severe combined immunodeficient) mice (effectively BALB/c congenic to B6 at the IgH locus, H-2$^{d/d}$) were bred with C57BL/6 Scid mice. The resulting Scid$_{F1}$ mice (D$^{b/d}$, K$^{b/d}$, L$^{d+}$) were either sublethally irradiated (2Gy) or non-irradiated and used as recipients. To study the anti-GVHD and leukemia effect of L$^d$-mismatched lymphocytes in normal mice, (B6×dm2)$_{F1}$ mice (H-2$^{b/d}$, L$^{d-}$) were used as lymphocyte donors and lethally irradiated (8.5 Gy) (B6×BALB/c)$_{F1}$ mice (H-2$^{b/d}$, L$^{d+}$) were used as recipients.

Infusion of allogeneic lymphocytes and tumor cells. Single viable cell suspensions were prepared from the spleen and lymph nodes of donor mice or from in vitro cultured DN Tr cell lines and injected into sex-matched recipient mice via the tail vein. Each mouse received either 4×10$^7$ spleen cells or varying doses (2–5×10$^6$/mouse) of DN Tr cells.

Tumor cell inoculation. To study the effect of GvL, cells of the A20 cell line (from ATCC), a B cell leukemia/lymphoma of BALB/c origin (Kim et al. (1979); Zeis et al. (1994)), was used. To determine the number of A20 tumor cells needed to cause lethal tumor development in naive Scid$_{F1}$ mice, different numbers of A20 cells (5×10$^3$, 10$^4$, 5×10$^4$, 10$^5$ and 10$^6$/mouse) were injected i.v. into Scid$_{F1}$ mice. The mice were observed daily for symptoms of morbidity and mortality. Groups of A20 cell recipient mice were killed at various time points after injection of leukemia cells for histologic evaluation to confirm that death was due to lymphoma. The inventors found that injection of 10$^5$ cells/mouse A20 cells was required to induce death of all injected mice between 4–6 weeks. This dose was thus used as the optimum dose for the subsequent experiments. A20 tumor cells were administered either alone or together with allogeneic splenocytes or DN Tr cell lines.

Evaluation of GVHD and tumor burden. To monitor signs of GVHD, the weights of each mouse were measured 3 times weekly. Other clinical signs of GVHD such as diarrhoea, ruffled fur, hunched posture, and scaled ears were also monitored. In addition, some mice were sacrificed for histologic evaluation of GVHD at different time points. Tissue samples were harvested from recipient mice before and after injection of donor cells and/or tumor cells. Tissues were fixed in 10% buffered formalin, sectioned (5 μm thick), stained with hematoxylin and eosin, and evaluated by light microscopy for GVHD and tumor infiltration. Each of the four major sites of GVHD involvement (hepatic parenchyma, biliary system, small intestine and colon) were scored on a scale of 0–10, thus giving a cumulative GVHD score ranging from 0–40. Each organ was evaluated for lymphocytic infiltration (score of 0–5), and evidence of parenchymal necrosis (score of 0–5) according to standard methods (Fowler et al. (1996)). For evaluation of tumor burden, major organs such as liver, spleen, lung, heart, kidney, intestine and lymph nodes were examined for the presence of tumor cell infiltration. Lethality was also monitored daily.

Cell Surface Marker Staining. Splenocytes from reconstituted mice were collected at various time points following reconstitution and triple stained with fluorescence-conjugated mAb specifically recognizing the αβ-TCR (1B2, FITC conjugated), CD4 (PE conjugated), CD8 (Cychrome Conjugated). In some mice staining was also performed using mAbs that recognized CD3 (FITC conjugated) and NK1.1 (PE conjugated). All mAbs except 1B2 were purchased from PharMingen. Data were acquired and analyzed on an EPICS* XL-MCL flow cytometer (COULTER CORPORATION, Miami, Fla.).

Suppression assay. $L^d$-specific CD8$^+$ responder cells (1000/well) were stimulated by irradiated BALB/c splenocytes (20 Gy). DN T cells were purified from the spleen of lethally irradiated (B6×BALB/c)$_{F1}$ mice 30 weeks after infusion of (B6×dm2)$_{F1}$ spleen cells, and used as putative suppressor cells. Varying numbers of DN T cells were added to the cultures. After 3 days 1µCi of [$^3$H]-TdR was added to each well, and the cells were harvested 18 hours later. Proliferation was measured using a Top Count (Packard) syntillation counter.

Cytotoxicity assays. Target cell death resulting from co-culture with DN T cells was measured as previously reported (Zhang et al. (1996); Matzinger (1991)). Briefly, purified DN T cells were stimulated by irradiated allogeneic splenocytes for 2–3 days in the presence of 30U/ml IL-2 and 50U/ml IL-4. Viable cells were harvested and seeded into 96-well microtiter plates as effector cells. 1B2$^+$CD8$^+$ target cells were stimulated with irradiated (20 Gy) (B6×BALB/c)$_{F1}$ splenocytes for 2–3 days, and labeled with 10 µCi/ml of [$^3$H] TdR at 37° C. overnight and used as targets. Tumour target cells were labeled in the same manner as CD8$^+$ T cells. After co-culture with the DN effector cells at 37° C. for 18 hours (in the presence of fresh irradiated allogeneic splenocytes when CD8$^+$ T cells were used as targets, and in the absence of fresh splenocytes when tumour cells were used as targets), the cells were harvested and counted in a beta syntillation counter. Specific cell lysis was calculated using the equation: % Specific killing=(S−E)/S×100, where E (experimental) is cpm of retained DNA in the presence of effector cells, and S (spontaneous) is cpm of retained DNA in the absence of effector cells.

Results

1. Infusion of MHC Class I $L^d$-mismatched Allogeneic Splenocytes Protect Immunodeficient Mice From Developing Lymphoma Without Causing GVHD.

Figure 1:
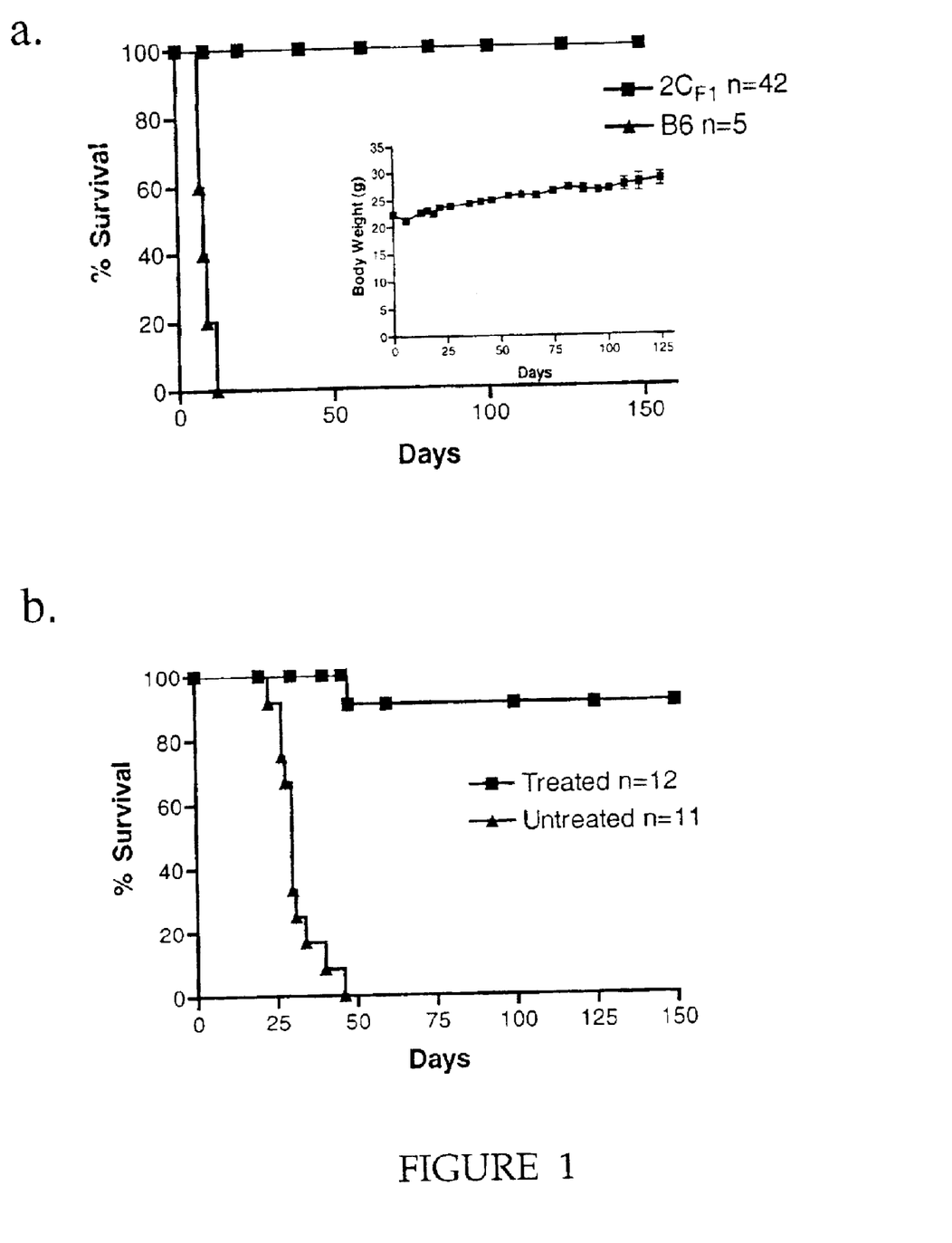
FIG. 1: (a) Absence of GVHD after reconstitution with $L^d$-mismatched splenocytes. Scid$_{F1}$ mice were sublethally irradiated with 2 Gy of irradiation. The next day mice were injected with $3\times10^7$ spleen cells from either $L^d$ mismatched $2C_{F1}$ (n=42) mice, or fully allogeneic lymphocytes from B6 (n=5) mice. Survival of the recipients was monitored for more than 150 days, and the body weights of mice reconsitituted with $2C_{F1}$ lymphocytes was measured weekly for 125 days (insert). (b) Leukemia and GVHD-free survival of recipient mice after being challenged with A20 lymphoma. Scid$_{F1}$ mice were either injected intravenously with a lethal dose of A20 tumour cells ($10^5$ cells/mouse) alone (untreated, ▼, n=11) or together with $3\times10^7$ $2C_{F1}$ spleen cells (treated, ■, n=12). Survival of the recipient mice was monitored for over 150 days.

To study whether encounter with one class I alloantigen in vivo leads to tolerance of infused donor lymphocytes to the host rather than causing GVHD, non-irradiated or sublethally irradiated (2Gy) Scid$_{F1}$ mice were injected intravenously with 4×10$^7$ viable spleen cells from 2CF1 mice. In this system, the donors and the recipients were mismatched for only $L^d$, and the anti-$L^d$ transgene can be detected by the monoclonal antibody 1B2. The expected immune response would be 1B2$^+$CD8$^+$ cells from the lymphocyte donor reacting to $L^d$ expressed on the recipient mice. All the control C.B-17 Scid mice injected with fully allogeneic B6 lymphocytes (n=5) developed an acute GVHD as evidenced by hunched posture, ruffled fur, sever diarrhoea, weight loss and died within 2 weeks after infusion of fully mismatched allogeneic lymphocytes. Histology study revealed typical acute GVHD (not shown). In contrast, none of the Scid$_{F1}$ mice (n=42) that received $L^d$ mismatched allogeneic lymphocytes lost weight (FIG. 1a, insert) or showed any clinical signs of GVHD. They remained healthy for the period of study (>150 days) (FIG. 1a). No difference was observed between irradiated and non-irradiated mice.

Figure 2:
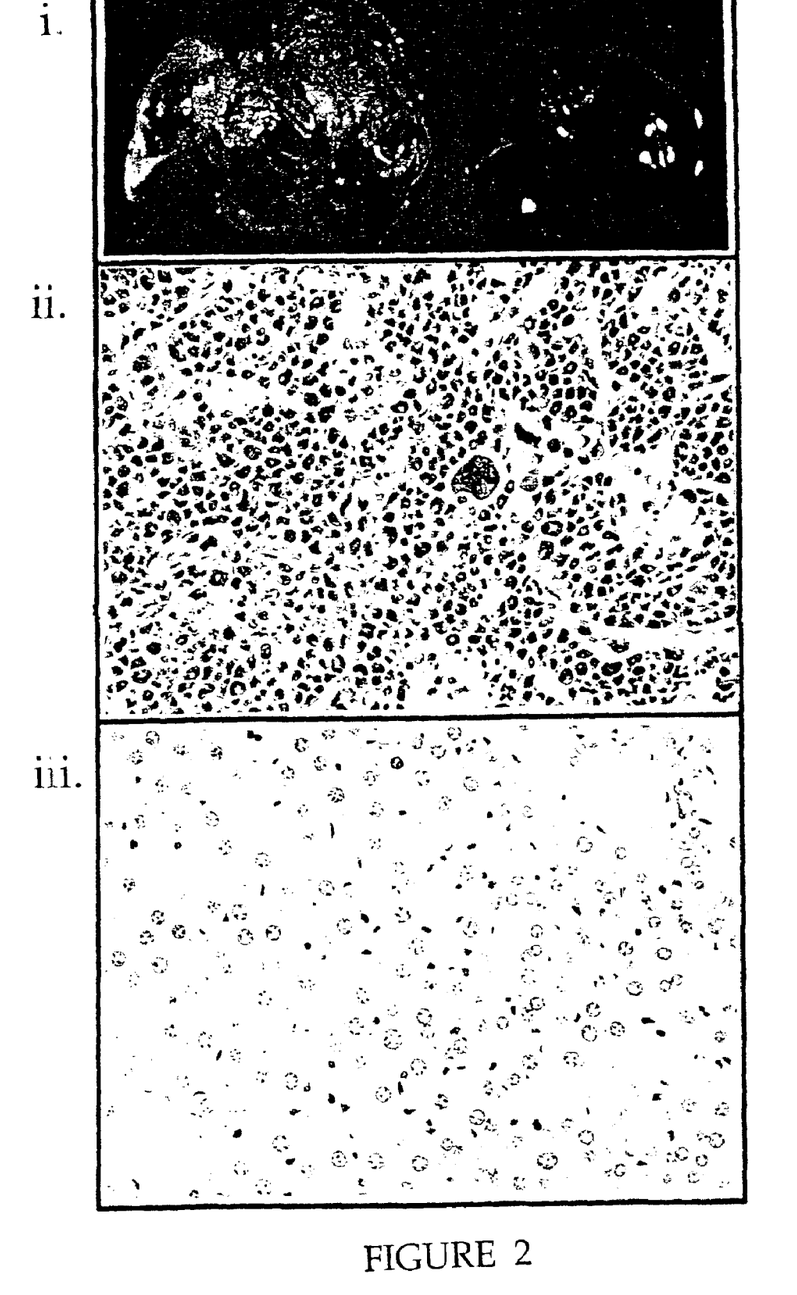

Next, the inventors investigated whether the infused allogeneic lymphocytes that have developed tolerance to the host $L^d$ antigen can mediate an anti-lymphoma response in the recipients. Scid$_{F1}$ mice were infused with a lethal dose of syngeneic A20 tumour cells, a cell line which initially arose spontaneously from BALB/c mouse (Kim et al. (1979)). One group of mice was injected with allogeneic 2C$_{F1}$ lymphocytes together with A20 tumour cells, and the other group of mice was given the A20 infusion alone. Both groups of mice were monitored initially twice a week for 3 weeks and then daily for lethality. As shown in FIG. 1b, all the Scid$_{F1}$ mice that were injected with tumour cells alone died of lymphoma between 28–42 days (median survival time 32 days, n=11) after injection of tumour cells. Those that died were autopsied and all were found to have lymphoma. The livers were greatly enlarged and diffusely infiltrated by tumour cells (FIG. 2(i), left). Histopathologic studies revealed a very diffuse infiltration in the liver by large malignant tumour cells which completely replaced the normal liver structure (FIG. 2(ii)). Malignant cells were also found in the spleen and lymph nodes, but not in lung, heart or kidneys (not shown). In striking contrast, 11 of 12 Scid$_{F1}$ mice that received the same number of A20 tumour cells plus a single dose of $L^d$-mismatched 2C$_{F1}$ lymphocytes on the day of tumour cell inoculation remained healthy for the period of study (>150 days) (FIG. 1b). A normal histological appearance was observed in all the major organs that had been examined (FIG. 2(i), right). Neither tumour infiltration nor GVHD was found in any organ of these animals (FIG. 2(iii)). When the recipients were rechallenged with a lethal dose of A20 tumour cells at 60 days after initial infusion of A20 and donor cells, these mice remained tumour free for more than 100 days (not shown). Therefore, a profound anti-tumour ability had been established in immunodeficient mice without causing GVHD. These data clearly demonstrate that infusion of mature splenocytes mismatched for one class I antigen $L^d$ with recipients does not cause GVHD, yet can protect the recipient from dying of lymphoma.

2. Infusion of $L^d$-mismatched Donor Lymphocytes Provoke GVL in the Absence of GVHD in Normal Mice.

Figure 3:
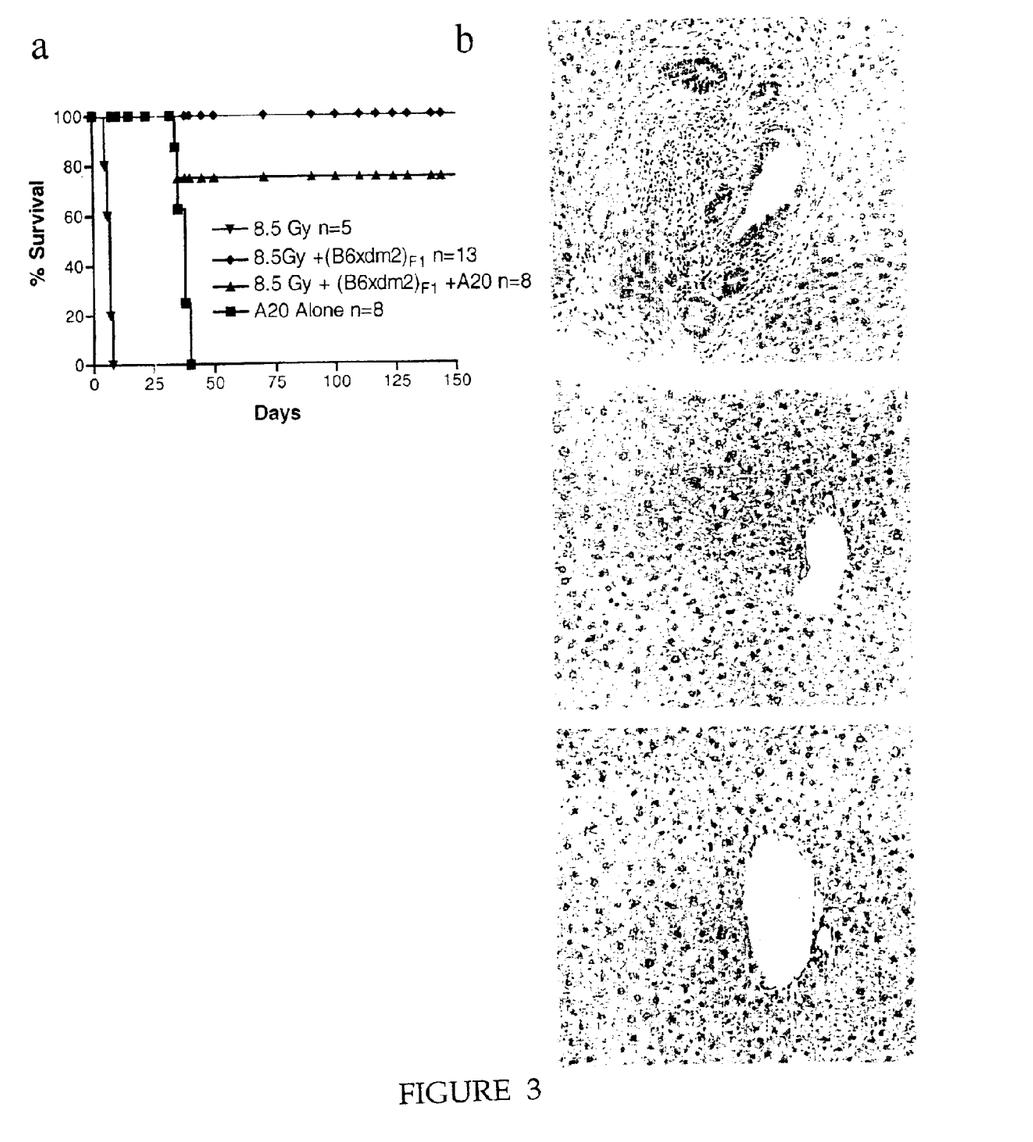

The above observations are based on a transgenic-Scid model. This model, although very useful for monitoring the fate and functional properties of anti-host T cells and delineating mechanisms involved in GVHD and GVL, might not be representative of true pathophysiological responses. To validate the above findings in normal mice, lethally (8.5 Gy) irradiated (B6×BALB/c)$_{F1}$ mice (D$^{b/d}$, K$^{b/d}$, L$^d$) were used as recipients, and (B6×dm2)$_{F1}$ mice (D$^{b/d}$, K$^{b/d}$, L$^{dm2}$) were used as lymphocyte donors. In this setting, there is also only one MHC class I (L$^d$) mismatch between donor and recipient. This mimics the system used in the above studies but avoids using both transgenic and Scid mice. Lethally irradiated (B6×BALB/c)$_{F1}$ mice were infused intravenously with a single dose (4×10$^7$/mouse) of viable splenic cells from sex-matched (B6×dm2)$_{F1}$ mice or were irradiated without the infusion of any cells (n=5) as controls. Additionally, (B6×BALB/c)$_{F1}$ mice were reconstituted with semi-allogeneic B62C splenocytes as a positive control for GVHD. Survival and GVHD were monitored three times a week. All lethally irradiated (B6×BALB/c)$_{F1}$ mice that were not given any treatment died within 1 week after irradiation and the (B6×BALB/c)$_{F1}$ mice that were reconstituted with semi-allogeneic B62C cells developed chronic GVHD (FIG. 3b, top). All 8 mice infused with $L^d$ mismatched splenic cells from (B6×dm2)$_{F1}$ mice survived over 180 days without weight loss or any clinical sign of GVHD (FIG. 3a), as seen in the transgenic-Scid model. Histology studies at various time points after infusion of allogeneic lymphocytes indicated no signs of GVHD in liver (FIG. 3b, middle), skin and small intestine (not shown).

Furthermore, the ability of normal mice to prevent the onset of leukemia was also evaluated. (B6×BALB/c)$_{F1}$ mice were irradiated and infused with 10$^5$ A20 syngeneic lymphoma cells together with $L^d$ mismatched (B6×dm2)$_{F1}$ splenocytes. Control animals that were infused with A20 alone died between 5–6 weeks after infusion of A20 syngeneic lymphoma cells. In contrast, six of the 8 mice that were infused with both (B6×dm2)$_{F1}$ spleen cells and A20 tumour cells enjoyed tumour-free survival for over 180 days. These animals showed no signs of GVHD or tumour burden (FIG. 3a, 3b middle). When normal (B6×BALB/c)$_{F1}$ mice were infused with $2C_{F1}$ trangenic cells together with A20 lymphoma, the same results were observed. (FIG. 3b, bottom). Together, these findings in normal mice confirm the findings in the transgenic-Scid$_{F1}$ model, and demonstrate that although infusion of fully or semi-allogeneic splenocytes results in GVHD in recipient animals, infusion of MHC class I $L^d$-mismatched lymphocytes helps immune-incompetent animals to reject tumour without causing GVHD.

4. 1B2$^+$DN T Cells Expand in vivo and Can Suppress Proliferation of Anti-host CD8$^+$ T Cells.

Figure 4:
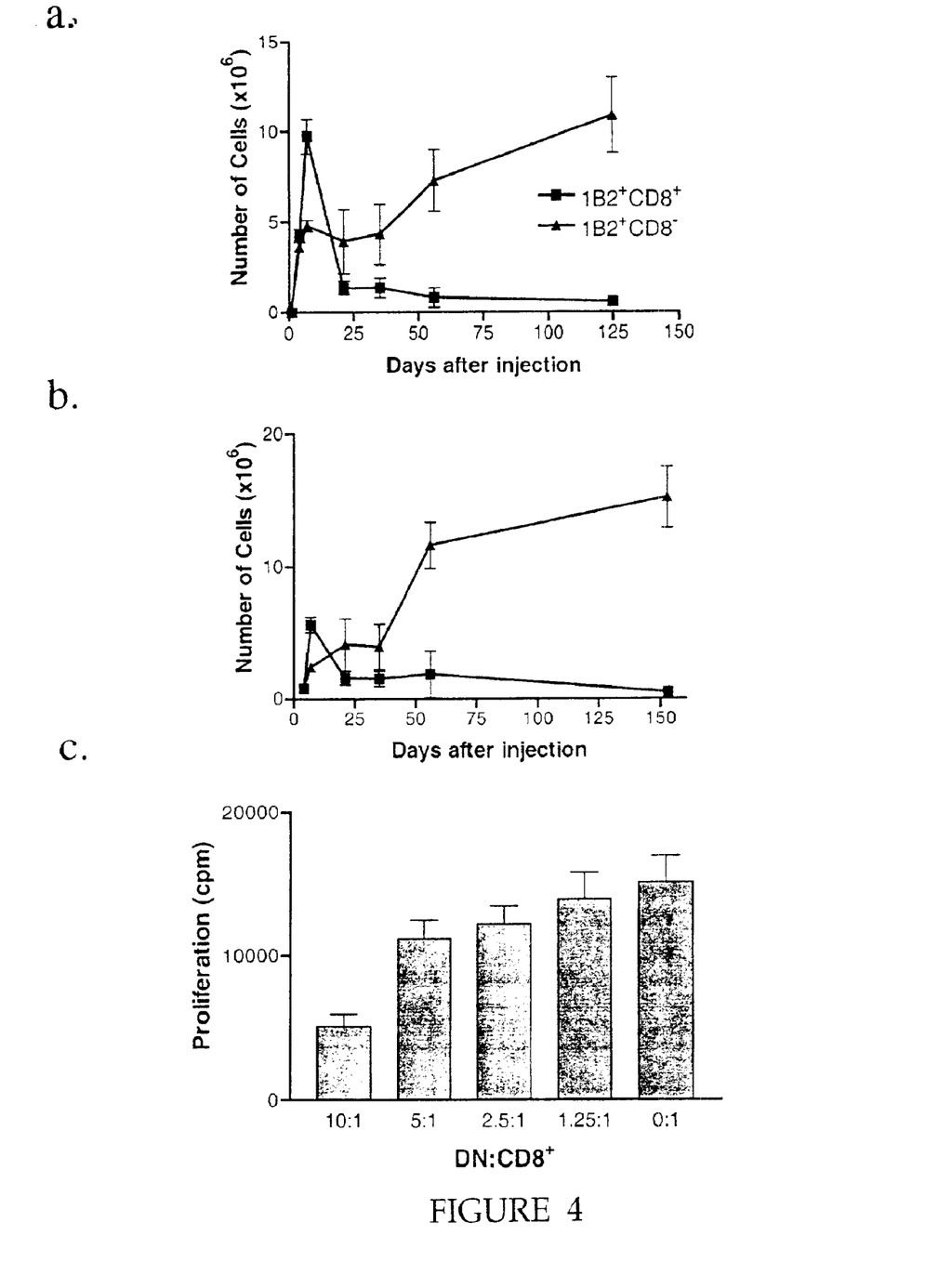

In order to understand the mechanism by which donor T cells mount an effective anti-tumour response in the absence of GVHD, the inventors monitored the fate of infused donor T cells in recipient mice. Due to the lack of specific markers for the identification of donor T cells in the host in normal (non-transgenic) animals, the transgenic-Scid model was used. Scid$_{F1}$ mice were infused with $2C_{F1}$ splenocytes either alone or together with A20 tumour cells. At various time points after infusion, the spleen and lymph node cells were double stained for anti-host TCR (with 1B2-FITC) and CD8-PE and analyzed by flow cytometry. The total number of 1B2$^+$CD8$^+$ and 1B2$^+$CD8$^-$ T cells were calculated. As shown in FIG. 4a, a vigorous expansion followed by a massive depletion of anti-host 1B2+CD8+ cells was observed in the periphery of recipients (Zhang et al. (1996); Yu et al. (1999)). Interestingly, the number of 1B2+CD8− T cells steadily increased to >30 fold at 8 weeks after infusion. Since these mice have few (<5%) 1B2$^+$CD4$^+$ T cells (Sha et al. (1988), this population is mostly 1B2$^+$DN T cells. Unlike the 1B2$^+$CD8$^+$ T cells, the 1B2$^+$CD8$^-$ T cells remained elevated for the period of study (>120 days) (FIG. 4a). Similar kinetic changes were observed in ScidF1 mice infused with both 2CF1 and A20 cells (FIG. 4b), and the increase in 1B2+CD8− cells was even more pronounced.

To determine whether the in vivo expanded DN cells are involved in inhibiting anti-host response, at 30 weeks after infusion of anti-$L^d$ cells, spleens were harvested from $L^{d+}$ recipients and triple stained with CD3, CD8 and CD4. CD3$^+$CD4−CD8− T cells were purified by FACS and their ability to suppress the proliferation of naive anti-host CD8$^+$ T cells was measured in vitro. As shown in FIG. 4c, the purified splenic CD3$^+$DN T cells inhibit the proliferation of anti-$L^d$ CD8$^+$ T cells in a dose-dependent manner, indicating that the in vivo expanded DN T cells can down-regulate anti-host responses mediated by CD8$^+$ T cells. This finding, together with the kinetic studies shown in FIG. 4a and b suggest that infusion of $L^d$-mismatched whole spleen cells leads to a selective expansion of DN T cells which prevents GVHD by suppressing anti-host CD8$^+$ T cells.

5. In vitro Generated 1B2$^+$DN Tr Cells Kill Both Anti-host T Cells and Lymphoma Cells.

Figure 5:
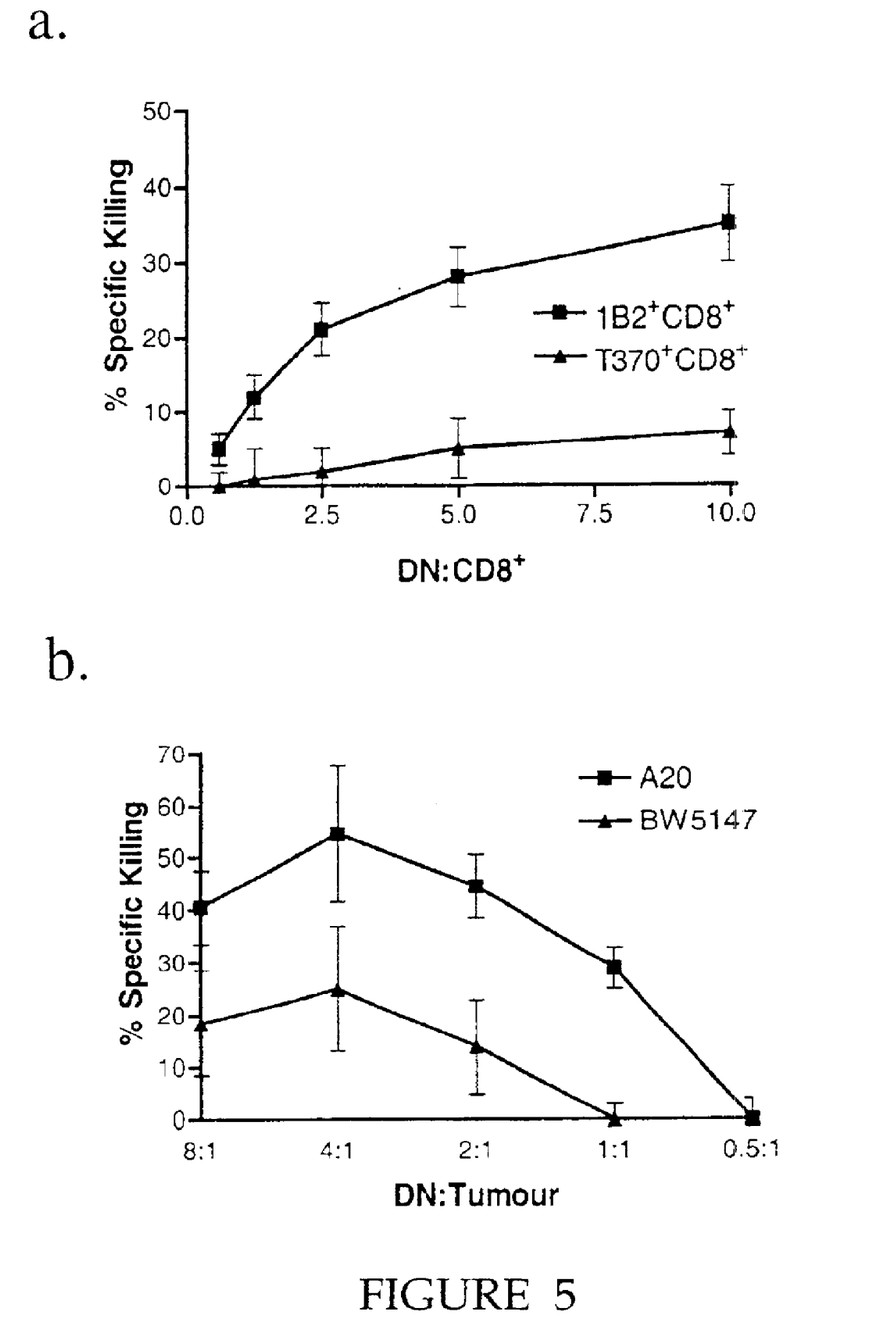

Although the inventors have demonstrated that infusion of one MHC class I mismatched donor lymphocytes leads to an anti-tumour effect in the absence of GVHD, the availability of this type of donor in humans can be limited. To explore the possibility of using in vitro generated DN T cells for the treatment of lymphoma, the inventors generated a panel of $L^d$-specific 1B2$^+$DN Tr cell lines from the spleen of $2C_{F1}$ mice. To elucidate the role of DN Tr cell lines in preventing GVHD, the 1B2$^+$DN T cell lines were used as effectors, and activated 1B2$^+$CD8$^+$ anti-host T cells were used as targets. Activated HY-specific CD8$^+$ T cells served as a 3rd-party control. The inventors demonstrate that 1B2$^+$DN Tr cell lines can specifically kill activated syngeneic anti-$L^d$ CD8$^+$ T cells in a dose dependant manner, but not CD8$^+$ T cells that carry a different TCR specificity (FIG. 5a). This result is consistent with the inventors in vivo finding that 1B2+CD8+ T cells are eliminated from the periphery of recipient mice (Zhang (1996)) (FIG. 4), and that recipient mice do not develop GVHD.

The finding that DN T cells increase more substantially in the spleen of reconstituted mice that were challenged with A20 lymphoma (FIGS. 4a and b) suggests that these cells also have an anti-lymphoma capability. To study the ability of vitro activated DN T cell lines to kill tumour cells, 1B2$^+$DN T cells were used as effector cells, and their ability to kill either $L^{d+}$A20 tumour cells (antigen-specific), or BW5147 tumour cells (H-2$^{K+}$, 3rd-party control) was determined by the JAM cytoxicity assay (Matzinger (1991)). As shown in FIG. 5b, the 1B2$^+$DN T cells lysed $L^{d+}$ A20 lymphomas in an antigen-specific and dose-dependant manner in contrast to a much lower cytotoxicity to BW5147 cells. Collectively, these data indicate that 1B2$^+$DN T cells can function as a double-edged sward to kill both syngeneic anti-host CD8$^+$ T cells and allogeneic lymphoma cells in vitro.

6. In Fusion of in vitro Generated 1B2$^+$DN T Cells Prevent Death Caused by Lymphoma Without Causing GVHD.

Figure 6:
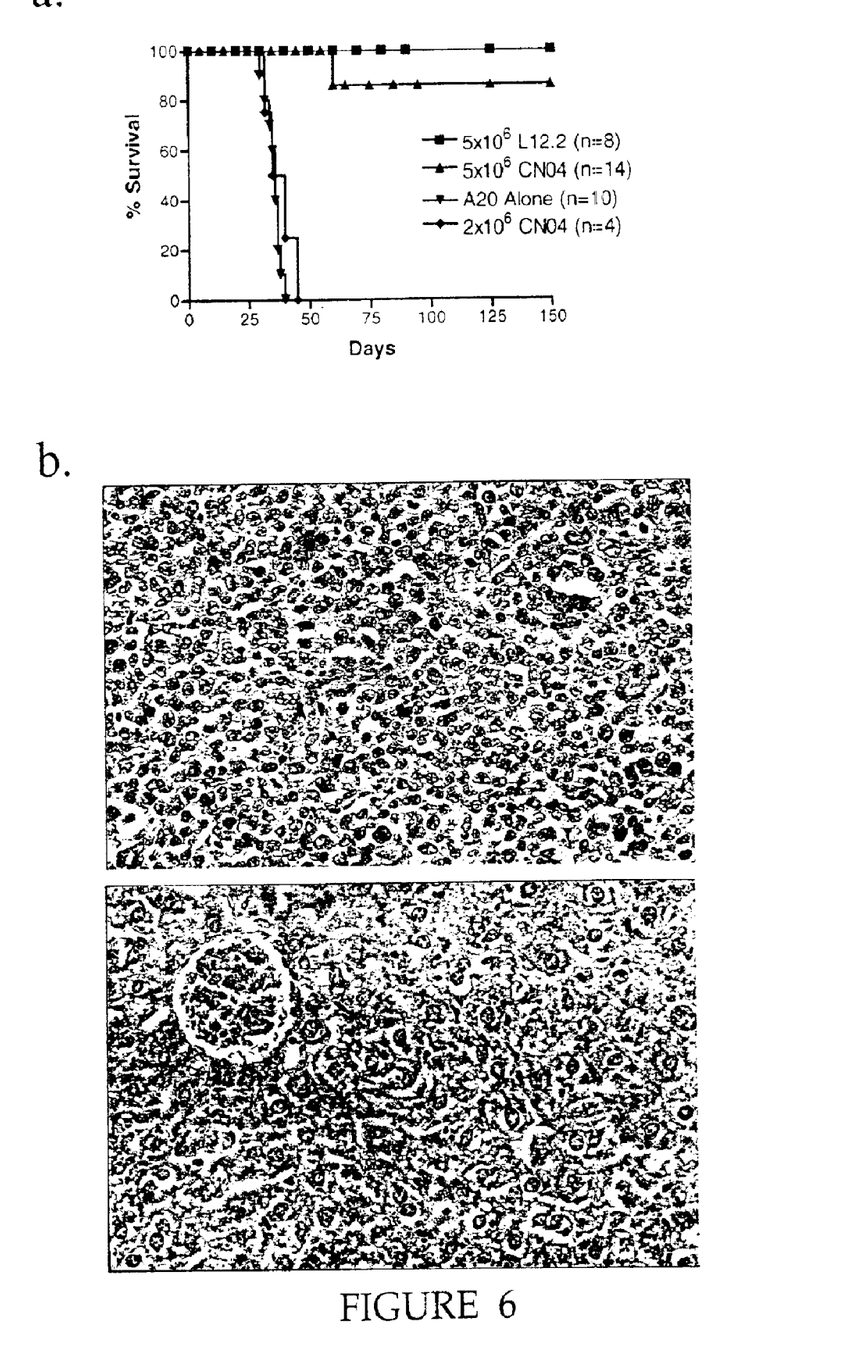

The inventors have demonstrated that the majority of T cells in the reconstituted animals are 1B2+DN, and that 1B2+DN T cells lines can kill A20 tumour cells. To determine whether infusion of in vitro activated allogeneic DN Tr cells alone can eliminate lymphoma cell in vivo without causing GVHD, (B6×BALB/c)$_{F1}$ mice were co-injected with varying doses of 1B2$^+$DN Tr cell lines together with a lethal dose of A20 tumour cells. As shown in FIG. 6a, all the mice that received A20 cells alone died of lymphoma between 32–38 days. Interestingly, although injection of $2 \times 10^6$ of DN Tr cells were not sufficient to prevent development of lymphoma, co-injection of $5 \times 10^6$ of the 1B2$^+$DN Tr cells with a lethal dose of A20 lymphoma prevented 14 out 15 mice from developing lymphoma. These mice lived for over 150 days with no detectable clinical or histopathological signs of lymphoma or GVHD (FIG. 6b). These data demonstrate that a single injection of in vitro produced $L^d$-mismatched DN Tr cells can effectively prevent death caused by lymphoma without inducing GVHD in the recipients, and suggest that the use of DN Tr cells may be a novel approach for the treatment of lymphoma and other cancers.

Discussion

In this Example, the inventors demonstrate, in both transgenic and normal mice, that although infusion of fully or semi-allogeneic lymphocytes causes GVHD, injection of immunodeficient or lethally irradiated mice with one MHC class I $L^d$-mismatched splenocytes does not result in clinical or pathological lesions of GVHD. More importantly, this treatment prevents the onset of lymphoma after being challenged with a lethal dose of tumour cells syngeneic to the host. In addition, the inventors also found that reconstituted irradiated (B6×DBA)$_{F1}$ mice with spleen cells from (B6× dm2)$_{F1}$ mice (mismatched for $L^d$ and multiple mHA with the recipients) resulted in indefinite GVHD free survival of the recipients (Young et al, in preperation), indicating that one MHC class I-mismatched donor lymphocytes can protect the development of GVHD caused by multiple mH mismatches.

In this Example, the inventors only presented data obtained from $L^d$-mismatched models. In a separate study the inventors found that infusion of B6 spleen cells into lethally irradiated B6$^{bm1}$ mice also resulted in more than 150 days survival of the recipients without GVHD (not shown). Together, these findings suggest that the outcome of bone marrow transplantation may be more favourable if one MHC locus-mismatched donors are used, since it not only protects recipients from developing GVHD, but also enhances the GVL capability of the graft. Infusion of one MHC class II locus mismatched lymphocytes has also been shown to significant prolong donor-specific skin graft survival (van Twuyver et al. (1990)).

The mechanism by which infusion of one MHC class I-mismatched donor lymphocytes leads to tolerance remains elusive. The inventors have demonstrated that: 1) Infusion of $L^d$-mismatched allogeneic lymphocytes leads to a selective activation and expansion of 1B2$^+$DN Tr cells in the hosts (FIGS. 4a and b). 2) A vigorous expansion followed by a massive apoptotic cell death occurred in the majority of activated anti-host 1B2$^+$CD8$^+$ cells in the periphery of the recipients after injection of $L^d$-mismatched spleen cells (FIG. 4a). 3) When the recipient mice were given a second injection of naïve 1B2$^+$CD8$^+$ T cells at 3 weeks after the first injection, no proliferation of the anti-host T cells could be detected, in contrast to the wave of proliferation seen 4–5 days after the first injection (Zhang et al. (1996)). 4) The in vivo expanded 1B2$^+$DN T cells can suppress 1B2$^+$CD8$^+$ T cell-mediated anti-host T cell response in vitro (FIG. 4c) 4) In vitro generated 1B2$^+$DN T cell lines can specifically kill activated anti-host CD8$^+$ T cells (FIG. 5a). Together, these results provide strong evidence to support the hypothesis that infusion of $L^d$-mismatched lymphocytes preferentially activates DN Tr cells which in turn suppress the response mediated by anti-host CD8$^+$ T cells and prevents the development of GVHD.

Whether GVHD and GVL are mediated by the same or different subset of T cells remains controversial (Horowitz et al. (1990); van Lochem et al. (1992); Apperley et al. (1986); Prentice et al. (1984); Horowitz et al. (1990); Pan et al. (1999)). This issue is central to the question of whether the beneficial effects of GVL can be separated from GVHD. Evidence provided in this Example indicates that the cells that cause GVHD and promote GVL are distinct. Using 2CF$_{F1}$ transgenic mice as donors, which allows the inventors to specifically identify and monitor anti-host T cells in the recipients, the inventors demonstrate that more than 90% of the recipients that received $L^d$-mismatched spleen cells gained anti-leukemia ability (FIG. 1b). The majority of T cells in these reconstituted recipients are 1B2$^+$DN T cells (FIG. 4b). When challenged with a second lethal dose of A20 tumour cells alone at 60 days after the initial injection of 2C$_{F1}$ and A20 cells, all the recipient mice survived tumour free for more than 100 days. Because at the time of the second tumour cell injection, most of the 1B2$^+$CD8$^+$ T cells have been eliminated, and the majority of T cells in the recipients are 1B2$^+$DN T cells (FIG. 4b), it is reasonable to suggest that 1B2$^+$DN T cells are directly involved in eliminating tumour cells. Furthermore, the inventors demonstrate that in vitro generated 1B2$^+$DN T cells are able to specifically kill $L^{d+}$ tumour cells in vitro, and that when infused together with a lethal dose of A20 lymphoma, the DN Tr cells are able to prevent leukemia onset and death of the recipients without causing GVHD (FIG. 6a). Together, these data demonstrate a direct role for DN Tr cells in eliminating allogeneic tumour cells, and suggest that anti-host and anti-tumour effects are mediated by different subsets of donor T cells. In addition, the inventors' findings also indicate the possibility of using in vitro generated DN Tr cells as a potential therapy for lymphoma, and perhaps other cancers either alone or in combination with a bone marrow transplant.

Figure 7:
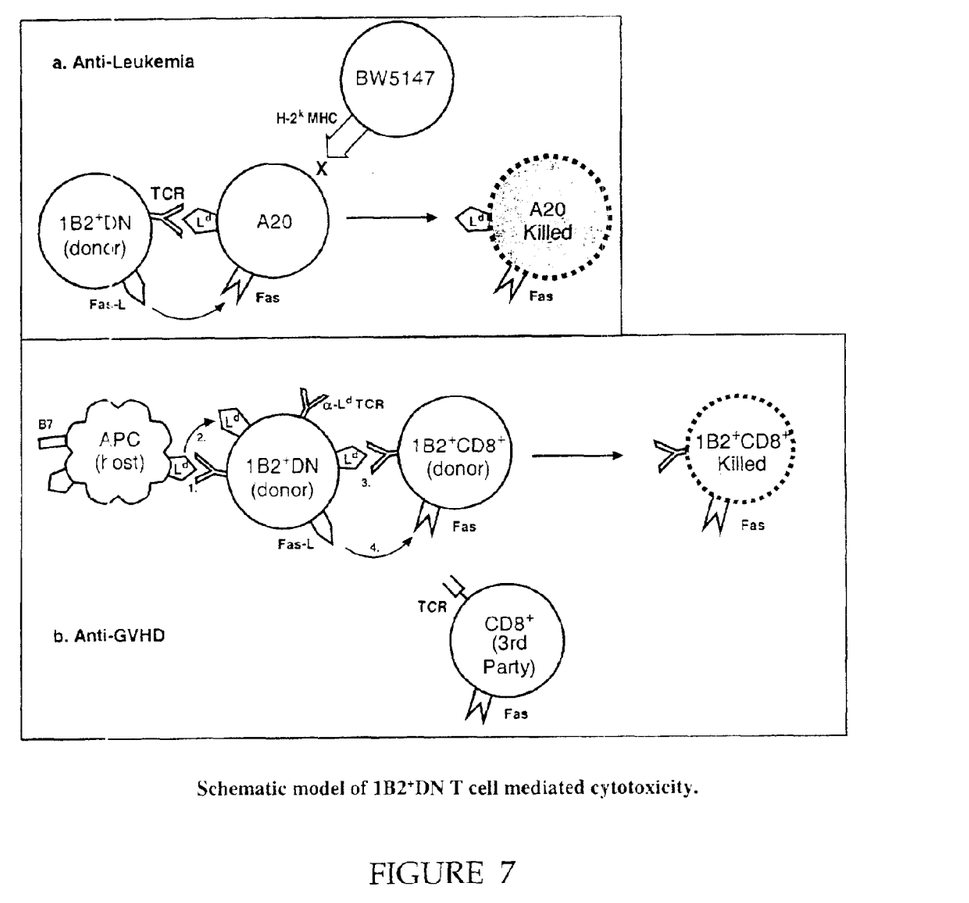
FIG. 7. Schematic model of DN T cell-mediated anti-GVHD and leukemia

How the same T cell could kill both allogeneic tumour cells and syngeneic anti-host T cells is an enigma. The inventors have shown previously that activated 1B2$^+$DN Tr cells express a high level of Fas ligand (Khan et al. (1999)). The inventors also demonstrated that 1B2$^+$DN Tr cells can acquire allo-MHC from antigen presenting cells and re-express the acquired allo-MHC on their own surface (Zhang et al. (2000)). Furthermore, the inventors have demonstrated that blocking either $L^d$ on DN Tr cells or TCR on CD8$^+$ T cells abrogates DN Tr cell mediated cytotoxicity to CD8$^+$ T cells (Zhang et al. (2000). Based on these findings, the inventors propose the following model to explain the dual role of DN Tr cells in preventing leukemia and GVHD (FIG. 7). Given that A20 cells constitutively express both $L^d$ and Fas (not shown), the anti-$L^d$ TCR on DN Tr cells could specifically recognize the $L^d$ expressed on the A20 cells. A subsequent ligation of Fas by Fas ligand on the DN Tr cells would deliver a death signal to the A20 tumour cells. This mechanism would explain the observed GVL effect mediated by anti-$L^d$ DN Tr cells. On the other hand, DN Tr cells could acquire $L^d$ through their anti-$L^d$ TCR from host antigen presenting cells. By expressing both $L^d$ and Fas ligand, DN Tr cells would be transformed into specific "killer antigen presenting cells". Once the TCR expressed on activated anti-host 1B2$^+$CD8$^+$ cells recognize the $L^d$ expressed on the DN Tr cells, the latter will send death signals to the former through Fas—Fas ligand pathways. CD8$^+$ T cells that carry a different TCR specificity, such as anti-HY T cells, will not recognize $L^d$ expressed on 1B2$^+$DN T cells and will therefore not be killed. This model explains how the DN Tr cell functions as a double-edged sword, able to kill both $L^{d+}$ tumour cells and anti-host T cells without impairing the ability of donor derived T cells to respond to other antigens.

Taken together, the present studies demonstrate that infusion of one MHC class I mismatched mature allogeneic lymphocytes leads to a selective expansion of DN Tr cells in the periphery of the recipients. The activated DN Tr cells have a dual function to kill both anti-host T cells and tumour cells, which results in a specific unresponsiveness to the host in vivo without impairing the immune responses to other antigen, including tumours.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

References:

Apperley, J. F. et al. Bone marrow transplantation for patients with chronic myeloid leukaemia: T-cell depletion with Campath-1 reduces the incidence of graft-versus-host disease but may increase the risk of leukaemic relapse. Bone Marrow Transplant. 1, 53–66 (1986).

Asano, M., Toda, M., Sakaguchi, N. & Sakaguchi, S. Autoimmune disease as a consequence of developmental abnormality of a T cell subpopulation. J. Exp. Med. 184, 387–396 (1996).

Ash, R. C. et al. Bone marrow transplantation from related donors other than HLA-identical siblings: effect of T cell depletion. Bone Marrow Transpl. 7, 443–452 (1991).

Barrett, A. J. & Malkovska, V. Graft-versus-leukemia: Understanding and using the alloimmune response to treat haematological malignancies. Br. J. Haematol. 93, 754–761 (1996).

Baxter, A. G., Kinder, S. J., Hammond, K. J. L., Scollay, R. & Godfrey, D. I. Association between abTCR+CD4–CD8– T-cell deficiency and IDDM in NOD/Lt mice. Diabetes 46, 572–582 (1997).

Born, W. et al. Immunoregulatory functions of gd-T cells. Adv. Immunol. 71, 77–144 (1999).

Bortin, M. M. & Rimm, A. A. Increasing utilization of bone marrow transplantation. II. Results of the 1985–1987 survey. Transplantation 48, 453–458 (1989).

Bushell, A., Niimi, M., Morris, P. J. & Wood, K. J. Evidence for immune regulation in the induction of transplantation tolerance: A conditional but limited role for IL-4. J. Immunol. 162, 1359–1366 (1999).

Chai, J.-G. et al. Anergic T cells act as suppressor cells in vitro and in vivo. Eur J Immunol 29, 686–692 (1999).

Champlin, R. et al. Retention of graft-versus-leukemia using selective depletion of CD8⁻positive T lymphocytes for prevention of graft-versus-host disease following bone marrow transplantation for chronic myelogenous leukemia. Transplant. Proc. 23, 1695–1696 (1991).

Champlin, R. E. Graft-versus-Leukemia without Graft-versus-Host Disease: An elusive goal of Bone Marrow Transplantation. Seminars in Hematology 29, 46 (1992).

Ciubotariu, R. et al. Specific suppression of human CD4⁺ Th cell responses to pig MHC antigens by CD8⁺CD28⁻ regulatory T cells. J. Immunol. 161, 5193–5202 (1998).

Cobbold, S. & Waldmann, H. Infectious tolerance. Curr. Opin. Immunol. 10, 518–524 (1998).

Drobyski, W. R., Vodanovic-Jankovic, S. & Klein, J. Adoptively transferred γδ-T cells indirectly regulate murine graft-versus-host reactivity following donor leukocyte infusion therapy in mice. J. Immunol. 165, 1634–1640 (2000).

Ferrara, J. L. & Deeg, H. J. Graft-versus-host disease. N. Engl. J. Med. 324, 667–674 (1991).

Fowell, D. & Mason, D. Evidence that the T cell repertoire of normal rats contains cells with the potential to cause diabetes. Characterization of the CD4⁺ T cell subset that inhibits this autoimmune potential. J. Exp. Med. 177, 627–636 (1993).

Fowler, D. H., Breglio, J., Nagel, G., Eckhaus, M. A. & Gress, R. E. Allospecific CD8⁺ Tc1 and Tc2 populations in graft-versus-leukemia effect and graft-versus-host disease. J. Immunol. 157, 4811–4821 (1996).

Gorczynski, R. M., Cohen, Z., Leung, Y. & Chen, Z. γδ-TCR+ hybridomas derived from mice preimmunized via the portal vein adoptively transfer increased skin allograft survival in vivo. J. Immunol. 157, 574–581 (1996).

Groux, H. et al. A CD4⁺ T-cell subset inhibits antigen-specific T-cell responses and prevents colitis. Nature 389, 737–742 (1997).

Han. H. S., Jun, H. S., Utsugi, T. & Yoon, J. W. A new type of CD4⁺ suppressor T cells completely prevents spontaneous autoimmune diabetes and recurrent diabetes in syngeneic islet-transplanted NOD mice. J. Autoimmune 9, 331–339 (1996).

Harrison, L. C., Dempsey-Collier, M., Kramer, D. R. & Takahashi, K. Aerosol insulin induces regulatory CD8 γδ-T cells that prevent murine insulin-dependent diabetes. J. Exp. Med. 184, 2167–2174 (1996).

Hauch, M. et al. Anti-leukemia potential of interleukin-2 activated natural killer cells after bone marrow transplantation for chronic myelogenous leukemia. Blood 75, 2250–2262 (1990).

Hori, S. S. et al. Tolerance induction of allo-class II H-2 antigen-reactive L3T4+ helper T cells and prolonged survival of the corresponding class II H-2-disparate skin graft. J. Immunol. 143, 1447 (1990).

Horowitz, M. M. et al. Graft-versus-leukemia reactions after bone marrow transplantation. Blood 75, 555–562 (1990).

Hsieh, B. et al. In vivo cytokine production in murine listeriosis. Evidence for immunoregulation by γδ+ T cells. J. Immunol. 156, 232–237 (1996).

Ierino, F. L., Yamada, K., Hatch, T., Rembert, J. & Sachs, D. Peripheral tolerance to Class I mismatched renal allografts in miniature swine: Donor antigen-activated peripheral blood lymphocytes from tolerant swine inhibit antidonor CTL reactivity. J. Immunol 162, 550–559 (1999).

Imamura, M., Hashino, S. & Tanaka, J. Graft-versus-leukemia effect and its clinical implications. Leukemia Lymphoma 23, 477–492 (1996).

Ke, Y. & Kapp, J. A. Oral antigen inhibits priming of CD8⁺ CTL, CD4⁺ T cells, and antibody responses while activating CD8⁺ suppressor T cells. J. Immunol. 156, 916–921 (1996).

Khan, Q., Penninger, J. M., Yang, L. M., Marra, L. E. K. I. & Zhang, L. Regulation of apoptosis in mature αβ+ CD4$^{31}$ CD8⁻ antigen-specific suppressor T-cell clones. J Immunol 162, 5860–5867 (1999).

Kim, K. J., Kannelopoulus-langevin, C., Mervin, R. M., Sachs, D. H. & Asofsky, R. Establishment and characterization of BALB/c lymphoma lines with B cell properties. J. Immunol. 122, 549–554 (1979).

Kolb, H. J. et al. Graft-versus-leukemia effect of donor lymphocyte transfusions in marrow grafted patients. Blood 86, 2041–2050 (1995).

Korngold, R. & Sprent, J. Surface markers of T cells causing lethal graft-vs-host disease to class I vs class II H-2 differences. J. Immunol. 135, 3004–3010 (1985).

Korngold, R., Leighton, C. & Manser, T. Graft-versus-myeloid leukemia responses following syngeneic and allogeneic bone marrow transplantation. Transplantation 58, 278–287 (1994).

Kranz, D. M., Tonegawa, S. & Eisen, H. N. Attachment of an anti-receptor antibody to non-target cells renders them susceptible to lysis by a clone of cytotoxic T lymphocytes. Proc. Natl. Acad. Sci. USA 81, 7922–7926 (1984).

Lancaster, F., Chui, Y. L. & Batchelor, J. R. Anti-idiotypic T cells suppress rejection of renal allografts in rats. Nature 315, 336–337 (1985).

Liu, Z., Tugulea, S., Cortesini, R. & Suciu-Foca, N. Specific suppression of T helper alloreactivity by allo-MHC class I-restricted CD8⁺. Int. Immunol. 10, 775–783 (1998).

Mason, D. & Powrie, F. Control of immune pathology by regulatory T cells. Curr. Opin. Immunol. 10, 649–655 (1998).

Matzinger, P. The JAM test A simple assay for DNA fragmentation and cell death. J. Immunol. Methods 145, 185–192 (1991).

Mayfield, R. S. et al. The mechanism of specific prolongation of class I-mismatched skin grafts induced by retroviral gene therapy. Eur. J. Immunol. 27, 1177–1181 (1997).

Palathumpat, V., Dejbakhsh-Jones, S., Holm, B. & Strober, S. Different subsets of T cells in the adult mouse bone marrow and spleen induce or suppress acute graft-versus-host disease. J. Immunol. 149, 808–817 (1992).

Palathumpat, V., Dejbakhsh-Jones, S. & Strober, S. The role of purified CD8⁺ T cells in graft-versus-leukemia activity and engraftment after allogeneic bone marrow transplantation. Transplantation 60, 355–361 (1995).

Pan, L. et al. Granulocyte colony-stimulating factor-mobilized allogeneic stem cell transplantation maintains graft-versus-leukemia effects through a perforin-dependent pathway while preventing graft-versus-host disease. Blood 93, 4071–4078 (1999).

Prentice, H. G. et al. Depletion of T lymphocytes in donor marrow prevents significant graft- versus-host disease in matched allogeneic leukaemic marrow transplant recipients. Lancet 1, 472–476 (1984).

Qin, S. et al. "Infectious" transplantation tolerance. Science 259, 974–976 (1993).

Roncarolo, M.-G. & Levings, M. K. The role of different subsets of T regulatory cells in controlling autoimmunity. Curr. Opin. Immunol 12, 676–683 (2000).

Sakaguchi, S., Takahashi, T. & Nishizuka, Y. Study on cellular events in post-thymectomy autoimmune oophoritis in mice. II. Requirement of Lyt-1 cells in normal female mice for the prevention of oophoritis. J. Exp. Med. 156, 1577–1586 (1982).

Sakaguchi, S. Regulatory T cells: key controllers of immunologic self-tolerance. Cell 101, 455–458 (2000).

Shiohara, T., Moriya, N., Hayakawa, J., Itohara, S. & Ishikawa, H. Resistance to cutaneous graft-vs.-host disease is not induced in T cell receptor d gene-mutant mice. J. Exp. Med. 183, 1483–1489 (1996).

Sha, W. C. et al. Positive and negative selection of an antigen receptor on T cells in transgenic mice. Nature 336, 73–76 (1988).

Sha, W. C. et al. Selective expression of an antigen receptor on CD8-bearing T lymphocytes in transgenic mice. Nature 335, 271–274 (1988).

Sprent, J., Schaefer, M., Lo, D. & Korngold, R. Properties of purified T-cell subsets. II. In vivo responses to class I vs class II H-2 differences. J. Exp. Med. 163, 998–1011 (1986).

Strober, S. et al. Double negative (CD4−CD8− ab+) T-cells which promote tolerance induction and regulate autoimmunity. Immunol. Rev. 149, 217–230 (1996).

Sun, D., Whitaker, J. N. & Wilson, D. B. Regulatory T cells in experimental allergic encephalomyelitis. I. Frequency and specificity analysis in normal and immune rats of a T cell subset that inhibits disease. Int. Immunol. 11, 307–315 (1999).

Suri-Payer, E., Amar, A. Z., Thornton, A. M. & Shevach, E. M. $CD4^+CD25^+$ T-cells inhibit both the induction and effector function of autoreactive T-cells and represent a unique lineage of immunoregulatory cells. J. Immunol. 160, 1212–1218 (1998).

Sykes, M., Harty, M. W., Szot, G. L. & Pearson, D. A. Interleukin-2 inhibits graft-versus-host disease-promoting activity of $CD4^+$cells while preserving $CD4^-$ and $CD8^-$ mediated graft-versus-leukemia effects. Blood 83, 2560–2569 (1994).

Szczepanik, M. et al. $\gamma\delta$-T cells from tolerized $\alpha\beta$-T cell receptor (TCR)-deficient mice inhibit contact sensitivity-effector T cells in vivo, and their interferon-g production in vitro. J. Exp. Med. 184, 2129–2139 (1996).

van Lochem, E., de Gast, B. & Goulmy, E. In vitro separation of host specific graft-versus-host and graft-versus-leukemia cytotoxic T cell activities. Bone Marrow Transplantation 10, 181–183 (1992).

van Twuyver, E. et al. Allograft tolerance induction in adult mice associated with functional deletion of specific CTL precursors. Transplantation 48, 844–847 (1989).

van Twuyver, E., Kast, W. M., Mooijaart, R. J. D., Melief, C. J. M. & de Waal, L. P. Induction of transplantation tolerance by intravenous injection of allogeneic lymphocytes across an H-2 class-II mismatch. Different mechanisms operate in tolerization across an H-2 class-I versus H-2 class-II disparity. Eur. J. Immunol. 20, 441–444 (1990).

Weiner, H. L. et al. Oral tolerance: immunologic mechanisms and treatment of animal and human organ-specific autoimmune diseases by oral administration of autoantigens. Annu. Rev. Immunol. 12, 809–837 (1994).

Wong, W., Morris, P. J. & Wood, K. J. Syngeneic bone marrow expressing a single donor class I MHC molecule permits acceptance of a fully allogeneic cardiac allograft. Transplantation 62, 1462–1468 (1997).

Yang, L. M., DuTemple, B., Gorczynski, R. M., Levy, G. A. & Zhang, L. Evidence for epitope spreading and active suppression in skin graft tolerance following donor specific transfusion. Transplantation 67, 1404–1410 (1999).

Yu, X. Z., Bidwell, S., Martin, P. J. & Anasetti, C. Visualization, fate, and pathogenicity of antigen-specific $CD8^+$ T cells in the graft-versus-host reaction. J. Immunol. 163, 4780–4787 (1999).

Zeis, M. et al. Induction of graft-versus-leukemia (GVL) activity in murine leukemia models after IL-2 pretreatment of syngeneic and allogeneic bone marrow grafts. Bone Marrow Transplant. 14, 711–715 (1994).

Zeis, M. et al. Allogeneic MHC-mismatched activated natural killer cells administered after bone marrow transplantation provide a strong graft-versus-leukaemia effect in mice. Br. J. Haematol. 96, 757–761 (1997).

Zhai, Y. & Kupiec-Weglinski, J. W. What is the role of regulatory T cells in transplantation tolerance? Curr. Opin. Immunol. 11, 497–503 (1999).

Zhai, Y. & Kupiec-Weglinski, J. W. What is the role of regulatory T cells in transplantation tolerance? Curr. Opin. Immunol 11, 497–503 (1999).

Zhang, Z. X., Yang, L. M., Young, K. J., DuTemple ,B. & Zhang, L. Identification of a previously unknown antigen-specific regulatory T cell and its mechanism of suppression. Nat. Med. 6, 782–789 (2000).

Zhang, L., Miller, R. G. & Zhang, J. Characterization of apoptosis-resistant antigen-specific T cells in vivo. J. Exp. Med. 183, 2065–2073 (1996).

Zhang, L. The fate of adoptively transferred antigen-specific T cells in vivo. Eur. J. Immunol. 26, 2208–2214 (1996).

We claim:

1. A method of inhibiting lymphoma cell growth or proliferation comprising administering an effective amount of a regulatory T-celi having the phenotype $CD3^+\alpha\beta$-$TcR^+$ $CD4^-CD8^-CD44^-CD28^-NK1.1^-$ to an animal in need of such treatment.

2. A method according to claim 1 wherein the regulatory T cells is expanded or activated in vitro prior to administration by culturing the cells with IL-2 and IL-4.

3. A method according to claim 2, further comprising culturing the cells with one class I mismatched allogeneic lymphocytes.

4. A method according to claim 1 wherein the regulatory T cells is expanded or activated in vitro prior to administration by culturing the cells in the presence of a tumor lymphona antigen.

5. A method according to claim 1 to treat lymphoma.

* * * * *